United States Patent [19]

Schmidt et al.

[11] Patent Number: 4,845,252

[45] Date of Patent: Jul. 4, 1989

[54] METHOD FOR THE CATALYTIC EPOXIDATION OF OLEFINS WITH HYDROGEN PEROXIDE

[75] Inventors: Manfred Schmidt, Gelnhausen; Guenter Prescher, Hanau; Johann Buchler, Darmstadt; Axel Kleemann, Muehlheim, all of Fed. Rep. of Germany

[73] Assignee: Degussa Aktiengesellschaft, Frankfurt, Fed. Rep. of Germany

[21] Appl. No.: 172,245

[22] Filed: Mar. 23, 1988

[30] Foreign Application Priority Data

Mar. 25, 1987 [DE] Fed. Rep. of Germany ....... 3709829

[51] Int. Cl.$^4$ ............................................ C07D 301/12
[52] U.S. Cl. ..................................... 549/531; 540/145
[58] Field of Search ....................... 549/531; 502/163; 540/145

[56] References Cited

FOREIGN PATENT DOCUMENTS 0633326 12/1961 Canada ............................. 549/531

OTHER PUBLICATIONS

Lendon, H. J.; Durbut, P, Varescon, F., *J. Am Chem. Soc.*, 103 pp. 3601–3603 (1981).
Renaud, J-P, Battioni, P., Bartoli, J. F., Mansay, D., *J. Chem. Soc. Chem. Commun.*, pp. 888–889 (1985).
Sheldon, R. A., *J Mol. Cat.*, 7, pp. 107–126, (1980).

*Primary Examiner*—Richard L. Raymond
*Assistant Examiner*—Mark W. Russell
*Attorney, Agent, or Firm*—Beveridge, DeGrandi & Weilacher

[57] ABSTRACT

A method for the catalytic epoxidation of olefines with hydrogen peroxide in the presence of tungsten oxo complexes or of a binuclear compound of the type μ-oxobis [porphyrinato-oxo tungsten (V)] or cis-oxo peroxo tungsten (VI) porphyrin or cis-dioxo porphyrinatotungsten (VI) with octaethyl porphyrin or 5,10,15,20-tetraphenyl porphyrin or 5,10,15,20-tetra(4-pyridyl)-porphyrin as ligands.

8 Claims, No Drawings

METHOD FOR THE CATALYTIC EPOXIDATION OF OLEFINS WITH HYDROGEN PEROXIDE

INTRODUCTION AND BACKGROUND

The present invention relates to a method for the catalytic epoxidation of olefines with hydrogen peroxide in the presence of a transition metal porphyrin complex in which a required charge equalization is performed by an anion.

Olefine oxides (oxiranes) are compounds which have significant importance in industry. They are used in the manufacture of lacquers, for preparing polyethers, polyurethanes, epoxide resins, detergents, glycols and a plurality of organic intermediate products (cf. U.S. Pat. No. 2,412,136 and DE-AS 11 39 477).

Various methods are already known in the art for the epoxidation of olefines. For example, oxiranes can be prepared according to the chlorohydrin method by reacting olefines with chlorine or sodium hypochlorite in alkaline medium and subsequently treating with bases. A primary disadvantage of this method is the formation of saline, environmentally damaging, waste water and of undesirable, chlorinated byproducts (cf. Ullmann's Enzyclopaedie der technischen Chemie (Ullmann's Encyclopedia of Technical Chemistry] vol. 10, p. 565 (3d. edition)).

A further known process is based on the reaction of olefines with organic hydroperoxides in the presence of a catalyst (cf. DE-AS 14 68 012). This second route of synthesis has the decisive disadvantage that due to the stoichiometry of the epoxidation reaction, the customarily expensive organic hydroperoxide (ROOH, wherein R is e.g. a lower-molecular group such as t-butyl or cumyl) is converted into large amounts of the corresponding alcohol (ROH) during the reaction according to the equation:

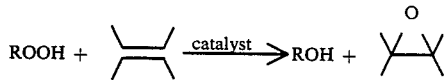

If the corresponding alcohol can not be utilized, it must be separated from the desired product of the reaction and removed or converted via several method stages into the corresponding hydroperoxide, thereby rendering the epoxidation method economically expensive.

Another method of synthesis is based on the use of organic peracids obtained by air oxidation of the corresponding aldehydes or from carboxylic acids with hydrogen peroxide (cf. BE- 535 068). The use of these organic percarboxylic acids is always associated with a risk due to their decomposability and therefore requires expensive precautionary measures as regards the performance of the method and the design of the equipment. In addition, large amounts of the corresponding carboxylic acids are always produced in epoxidations with organic peracids which carboxylic acids must be separated and removed or returned in a stoichiometric or excess stoichiometeric amount.

The described disadvantages can be eliminated by using hydrogen peroxide as the epoxidation agent, since according to theory only water should accumulate in addition to the epoxidation product. Since the reactivity of hydrogen peroxide is weak in relation to olefines, epoxidations are performed with this reagent in the presence of catalysts. Catalysts such as molybdenum compounds and tungsten compounds are suitable only for a few olefines. In this connection, see e.g. GB 837,464 in which the various metal catalysts described in "J.A.C.S.", vol. 59, pp. 2342 to 2344, 1937 are used, U.S. Pat. No. 2,786,854, in which tungstic acid is used, U.S. Pat. No. 2,833,787, in which acidic salts of metals of the VI group of the periodic system of the elements, e.g. of tungsten and molybdenum, are used, BE 860,776, in which tungsten-containing and molybdenum-containing compounds are used, U.S. Pat. No. 3,993,673, in which arsenic-containing catalysts are used, U.S. Pat. No. 3,953,362, in which a molybdenum-containing catalyst is used, U.S. Pat. No. 4,026,908 in which mercury derivatives plus a compound of molybdenum, tungsten, vanadium or titanium is used, U.S. Pat. No. 3,806,467, in which organic and inorganic tin compounds plus organic or inorganic compounds containing molybdenum, tungsten, vanadium, selenium or boron are used, Bull. Chem. Soc. Jap. 42, pp. 1604, 1969, in which selenium dioxide is used and U.S. Pat. No. 3,778,451, in which compounds of molybdenum, tungsten, vanadium, niboium, tantalum, uranium and rhenium are used.

These substances are catalytically active; however, for various reasons the methods which can basically be executed with them are not used in technology. In conjuction with hydrogen peroxide solutions, either the hydrogen peroxide is rapidly broken down by them or only an unsatisfactory epoxidation speed is achieved. Methods employing these catalysts are also problematic because, frequently rather large amounts of byproducts, such as diols and ketones, are formed in addition to the desired epoxidation product; the separation of which byproducts can pose considerable difficulties.

Experiments have also already been undertaken to carry out methods for the catalytic epoxidation of olefines with other epoxation agents using metal prophyrin complexes as catalysts. Epoxation agents used in this connection were compounds such as iodoso benzene (PhIO) (Groves, J. T.; Nemo, T. E.; Myers, R. S., J. Am. Chem. Soc., 101, p. 1032, 1979, alkali metal hypochlorite such as NaOCl or LiOCl (Guilmet, E.; Meunier, B.; Tetrahedron Lett. 1980, 4449) as well as organic hydroperoxides such as t-butyl hydroperoxide or cumol hydroperoxide (Ledon, H. J.; Durbut, P.; Varescon, F., J. Am. Chem. Soc. 103, 3601, 1981. Chloroiron (III)-tetraphenyl porphyrin (FeCl) (TPP), chloro-manganese (III)-tetraphenyl porphydrin (MnCl) (TPP) or chloro-chromium (III)-tetraphenyl porphyrin (CrCl) (TPP) have been suggested, for example, as metal catalysts suitable for reaction with these epoxidation agents. Manganese (III)-tetraphenyl porphyrin has also already been used with hydrogen peroxide as oxidation agent (Renaud, J. -P.; Battioni, P.; Bartoli, J. F.; Mansuy, D., J. Chem. Soc., Chem. Commun. 1985, 888). To be sure, these catalysts have a strong decomposing action on $H_2O_2$, so that the selectivities which can be achieved in regard to hydrogen peroxide are only very slight unless expensively substituted porphyrin ligands are used.

Oxo porphyrin complexes such as oxochloro(5,10,15,20-tetraphenyl porphyrin)-molybdenum (V) (O=Mo(TPP)Cl) have also been suggested in conjunction with organic hydroperoxides. However, an experiment to use hydrogen peroxide instead of an organic hydroperoxide with a catalyst of the composition oxo(5,10,15,20-tetraphenyl porphyrin)-molybdenum (V) methoxide for epoxidizing the olefin cyclohexene failed: No epoxidation could be observed (F. Varescon, thesis, The University of Claude Bernard-Lyon I, 1982).

SUMMARY OF THE INVENTION

It has now been found that the catalytic epoxidation of olefines with hydrogen peroxide succeeds with very high selectivity if the olefine is reacted in a homogeneous phase or in a two-phase system with hydrogen peroxide in the presence of tungsten oxo complexes or
a binuclear compound of the type -oxobis [porphyrinator oxo tungsten (V)] or
an oxo peroxo compound of the type cis-oxo peroxo tungsten (VI) porphyrin or
a cis-dioxo porphyrinato tungsten (VI) complex
with
octaethyl porphyrin or
5,10,15,20-tetraphenyl porphyrin or
5,10,15,20-tetra(4-pyridyl)-porphyrin as ligands in which hydrogen atoms or free electron pairs are optionally substituted once or several times on the phenyl or pyridyl groups by halogen, hydroxy, carboxy, cyano, rhodano, nitro, $C_1$-$C_6$-alkyl, trihalomethyl, $C_1$-$C_6$-alkoxy, $C_1$-$C_6$-alkane sulfonyloxy, amino carbonyl, amino carbonyl containing one or two $C_1$-$C_6$-alkyl groups, by $C_1$-$C_6$-alkyl carbonyl, amino, Di-$C_1$-$C_6$-alkyl amino, ($C_1$-$C_6$-alkyl)$_3$N, $C_1$-$C_6$-alkanoyl amino, $C_1$-$C_6$-alkyl-$C_1$-$C_6$-alkanoyl amino, $C_1$-$C_6$-alkane sulfonyl amino, $C_1$-$C_6$-alkyl-$C_1$-$C_6$-alkane sulfonyl amino sulfonyl, amino sulfonyl containing one or two $C_1$-$C_6$-alkyl groups, $C_1$-$C_6$-alkoxysulfonyl (—SO$_2$—O—$C_1$-$C_6$-alkyl), sulfo or $C_1$-$C_6$-alkane sulfonyl and two of these groups can also be the methylene dioxy group, whereby the complex in the case of tungsten oxo complexes optionally carries an anion on the central atom from the group $F^-$, $Cl^-$, $Br^-$, $I^-$, $CH_3O^-$, $C_2H_5O^-$, $C_3H_7O^-$, t—$C_4H_9O^-$, $HO^-$, $AcO^-$, $SCN^-$, $CN^-$, $C_6H_5O^-$.

The catalytic properties can be controlled and optimized, adapted to the particular olefine, by means of the steric and electronic effects of the specified substitutents on the phenyl or pyridyl group of the 5,10,15,20-tetraphenyl porphyrin or 5,10,15,20-tetra(4-pyridyl)-porphyrin.

The catalysts provided in accordance with the invention for carrying out the method are in part new substances. This includes all tungsten oxo complexes claimed for the method of the invention with the exception of those carrying $OH^-$, $CH_3O^-$ or $C_6H_5O^-$ as anion. The complexes already known are accessible in great purity according to known methods in the literature (J. W. Buchler et al., Chem. Ber., 1973, no. 106, p. 2710; Liebigs Ann. Chem., 1971, no. 745, p. 135; Inorg. Nucl. Chem. Lett., 1972, no. 8, p. 1073, K. Rohbock, dissertation, RTWH Aachen, 1972.

The various porphyrin ligands are prepared, to the extent that they are not commercially available, according to Adler et al., J. Org. Chem. no 32, p. 476, 1967 and Adler et al., J. Heterocyl. Chem. no. 5, p. 669, 1968 and freed of chlorine (porphyrin with a partially hydrated pyrrole member) if required (K. M. Smith et al., Tetrahedron Lett., No. 30, p. 2887, 1973).

The new substances under the tungsten oxo complexes described in the German parallel application reference no. P 37 09 831.4-44 filed at the same time (corresponding to U.S. patent application Ser. No. 07/172,325 filed Mar. 23, 1988) can be prepared only in part according to the known W(CO)$_6$ method.

Said parallel application P 37 09 831.4-44 discloses new methods of preparation for these new substances and their precursor which are also suitable for obtaining the already-known complexes claimed for the method of the invention. Accordingly, the corresponding U.S. application Ser. No. 07/172,325 filed Mar. 23, 1988 is relied on and incorporated herein.

The first synthesis path is shown by equation (1), the second synthesis path by equations (2a) and (2b) and the transfer of the complexes accessible in the second synthesis path with halogen as anion into the other complex compounds is shown by equation (3) (more detailed explanations can be found in parallel application P 37 09 831.4-44):

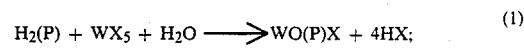

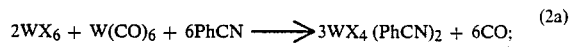

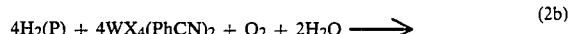

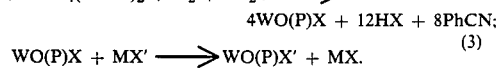

In the above equations:
P=porphyrin ligand, optionally substituted;
X,X'=any anion with simple negative charge;
M=alkali metal or proton.
Olefines according to the general formula

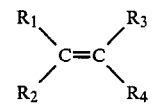

can be reacted according to the epoxidation method of the invention, whereby $R_1$ to $R_4$ can be identical or different and signify both hydrogen or a linear or branched alkyl group with 1 to 30 carbon atoms or signify a cycloalkyl group with 3 to 12 C atoms which can contain as heteroatoms e.g. one or more O, N or S atoms.

$R_1$ and $R_2$ or $R_3$ and $R_4$ can also be substituted by functional groups which are stable in the reaction environment such as e.g. by hydroxy, chloro, fluoro, bromo, iodo, nitro, methoxy, alkoxy, amino, carbonyl, ester, amido, nitrilo groups. They can also be unsaturated, that is, polyolefines such as e.g. dienes, trienes and other compounds with double bonds can also be used in the instant invention whether conjugated or not.

Under this precondition, the following can be considered among the olefines which can be epoxidized according to the instant method:

Ethylene, propylene, the butenes, butadiene, the pentenes, isoprene, hexene (1), hexene (3), heptene (1), octene (1), diisobutylene, nonene (1), tetradecene (1), pentamyrcene, camphene, undecene (1), dodecene (1), tridecene (1), tetradecene (1), pentadecene (1), hexadecene (1), heptadecene (1), octadecene (1), nonadecene (1), eicosene (1), the trimers and tetramers of propylene, the polybutadienes, the polyisoprenes, styrene, α-methyl styrene, divinyl benzene, indene, stilbene, cyclopentene, cyclohexene, cycloheptene, cyclooctene, cyclooctadiene, cyclododecene, cyclododecatriene, dicyclopentandiene, methylencyclopropane, methylencyclopentane, methlencyclohexane, vinyl cyclohexene, methallyl ketone, allyl chloride allyl bromide acryl acid, methacrylic acid, crotonic acid, vinylacetic acid, crotyl chloride, methallyl chloride, the dichlorobutenes, allyl alcohol, allyl carbonate, allyl acetatae, the alkyls of acrylates and methacrylates, diallyl maleate, diallyl phthalate, the unsaturated oils such as soy bean oil, the unsaturated fatty acids such as oleic acid, linolenic acid, balidinic acid, erucic acid, oleosteric acid, myristic acid, palmitic acid, ricinoleic acid, etc. and their esters.

An advantage of the invention is the fact that the hydrogen peroxide required herein as reactant can be used in all customary commercial forms, namely, in the form of aqueous hydrogen peroxide solutions with a hydrogen peroxide content of 30 to 90% by weight or as pure hydrogen peroxide, more sharply diluted hydrogen peroxide, water-free hydrogen peroxide dissolved in organic solvents or in the form of compounds which release hydrogen peroxide under the reaction conditions (metal peroxides such as magnesium peroxide or zinc peroxide as well as hydrogen peroxide addition compounds (peroxo hydrates), e.g. from sodium carbonate, sodium pyrophosphate and urea). Such compounds that release hydrogen peroxide under the conditions of the reaction can be readily determined.

It is especially advantageous if the reaction medium used is an organic solvent or a solvent mixture which permits a transition from hydrogen peroxide used as aqueous solution into the organic phase.

The following, for example, can be used as organic solvents for this purpose: Alkyl esters or cycloalkyl esters of saturated, aliphatic carboxylic acids with a carbon number of 4-8 (see, e.g. DE-PS 32 25 307, page 5), methylene chloride, dioxane, tert.-butanol, tetrahydrofurane, benzene, ethanol, chloroform and methanol. Mixtures of organic solvents can also be used.

Potential solvent mixtures are e.g. combinations of one or several of the above-named carboxylic acid esters with water, methylene chloride, dioxane, tert.-butanol, tetrahydrofurane, benzene, ethanol, chloroform and/or methanol.

An addition of alkyl esters or cycloalkyl esters of saturated, aliphatic carboxylic acids with a carbon number of 4-8 has proven to be especially useful for the solution of water-free hydrogen peroxide.

The amounts of catalyst added in the method of the invention which are to be used can be located within a wide range. The catalyst concentration to be used in the individual case can be selected in accordance with the type of tungsten-porphyrin compound chosen and provided according to the invention as well as in accordance with the reactivity of the particular olefine to be reacted. It lies in a concentration range which is generally 1/10000 to ½ mole, preferably 1/50000 to 1/5 mole per mole hydrogen peroxide.

Another object of the invention is the multiple usage of the catalyst used which can be used for further batches after suitable separation out of the reaction mixture. Thus, the catalyst can be recycled.

According to another advantageous embodiment of the invention, the selectivity rates, which are high in any case, can be improved by means of the addition of slight amounts, preferably from 0.1 to 10 moles of a heterocyclic amine, in relation to 1 mole of the catalyst. Of particular interest are equimolar amounts of a compound of the family of pyridine, such as 2,6-dimethyl pyridine, 2,6-ditertiary butyl pyridine, 3,5-dimethyl pyridine as well as the three picolines, the 4-halogenopyridines as well as the salts of 2,2-bipyridyl or of imidazole, e.g. imidazole itself. The concentration of the olefin in the reaction system is not critical, the molar ratio between olefin and hydrogen peroxide can be 1:30 to 30:1.

The reaction temperatures can be within a broad range. They depend on the particular activity of the catalyst used, the reactivity of the olefine used, the tendency of the desired oxirane to ring opening and the type of solvent. They range in general from 0 to 150, preferably 20 to 120 and especially from 20° to 80° C. The reaction times normally run from 10 minutes to 24 hours. The reactions can be performed under atmospheric pressure or at higher pressures as long as the reaction system can be maintained in a liquid phase.

The reaction is preferably performed in a pressure range between 1 and 50 bar.

The advantages obtainable with the invention are:
Very short reaction times
High selectivity (hardly any byproduct)
Low catalyst concentration
High chemical stability of the catalyst, especially in relation to the epoxidation agent
Slight or no $H_2O_2$ breakdown
Only water is produced from the epoxidation agent
Catalyst can be easily separated and reused.
Simple course of reaction synthesis

DETAILED DESCRIPTION OF INVENTION

The invention will be explained in more detail in the following illustrative examples.

Preliminary comment with regard to the individual examples:

The catalysts used in the examples of embodiments and obtainable in part according to the parallel application relied on above or according to the literature are used for the epoxidation of differing olefinic initial materials with hydrogen peroxide according to the invention as follows:

A solution of olefin, catalyst and solvent is prepared, heated to a temperature in a range of 20°-100° C. and reacted with hydrogen peroxide (30 to 90-% by wt.). This is version I. Alternatively, a solution of olefine, hydrogen peroxide (30 to 90% by wt.) and solvent is prepared and then reacted with catalyst; then, the mixture is caused to react with stirring and heat. This is version II.

In a variant which can be applied equally to versions I and II, a small amount of a heterocyclic amine, e.g. from the family of pyridine or imidazole is added to the components in a flask prior to the addition of the remaining component. In the case of the olefines added, the work can be performed under atmospheric pressure. Specimens are removed in the course of the reaction and analyzed for their content of epoxide or $H_2O_2$. The amount of formed epoxides is determined either by gas chromatography or titration and the amount of hydrogen peroxide by customary titration with cerium (IV) sulfate. The results obtained in the tests are apparent from the following table, whereby the selectivity is defined as follows:

$$\text{selectivity (\%)} = \frac{\text{mole formed epoxide} \times 100}{\text{mole reacted } H_2O_2}$$

| Example Nr. | Olefine (Mole(s)) | $H_2O_2$ (Mole(s)) | Catalyst | (Mole(s)) | Solvent (ml) | Reaction Temp. (°C.) | condition Time (h) | Conversion $H_2O_2$ | Selectivity (%) |
|---|---|---|---|---|---|---|---|---|---|
| 1 | 1,5-COD[1] (72) | 25,86% in nPAC[2] (24) | OW(TTP)CL[3] | $24 \times 10^{-2}$ | nPAC | 60 | 1 | 92,5 | 83,2 |
| 2 | 1,5-COD (72) | 25,86% in nPAC (24) | OW(TTP)CL* | $24 \times 10^{-2}$ | nPAC | 60 | 0,5 | 94,2 | 96,6 |
| 3 | 1,5-COD (72) | — | OW(TTP)CL | $24 \times 10^{-2}$ | nPAC | 60 | 1 | 0 | 0 |
| 4 | 1,5-COD (72) | 85% in $H_2O$ (24) | OW(TPP)Br[4] | $24 \times 10^{-2}$ | nPAC | 60 | 1 | 97,2 | 98,9 |
| 5 | 2-Methyl-2-buten (72) | 25,86% in nPAC (24) | OW(TPP)Br | $24 \times 10^{-2}$ | nPAC | 60 | 3 | 94,6 | 70,4 |
| 6 | 1,5-COD (72) | 25,86% in nPAC (24) | OW(TPP)Br | $24 \times 10^{-2}$ | nPAC | 60 | 1 | 96,1 | 86,5 |
| 7 | Cyclohexene (72) | 85% in $H_2O$ (24) | OW(TPP)Br | $24 \times 10^{-2}$ | tert. butanol | 60 | 1,5 | 83,3 | 81,1 |

[1] 1,5-cyclooctadiene
[2] acetic acid propyl ester
[3] TTP = 5, 10, 15, 20-tetra(p-tolyl)-porphyrin
[4] TPP = 5, 10, 15, 20-Tetraphenyl-porphyrin
*reuse of the catalyst according to example 1
**reference example The following further embodiments for the epoxidation of various olefines use catalytic substances whose preparation was compiled before the table of results.

EXAMPLE 8

Preparation of perchlorato-oxo[5,10,15,20-tetra(p-chlorophenyl)porphyrinato]tungsten (V), WO(Tp-ClPP)OClO$_3$ A solution of 232 mg (0.12 mmole) [WO(Tp-ClPP)]$_2$O in 15 ml CHCl$_3$ was compounded with 2 ml 7% aqueous HClO$_4$. The mixture was slightly heated under constant agitation until the CHCl$_3$ had evaporated. The precipitated complex was filtered off, washed neutral with distilled water and crystallized out of CHCl$_3$. 225 mg (88%) WO(Tp-ClPP)OClO$_3$ were obtained in the form of black crystals.
C$_{44}$H$_{24}$N$_4$Cl$_5$O$_5$W (1049.8).
Calculated: C 50.35 H 2.28 N 5.33; C:H=22.08; C:N=9.44 .
Found: C 45.77 H 1.99 N 4.74; C:H=23.0; C:N=9.65. Substance still contained aluminum oxide
UV/VIS ($\lambda$ max, log $\epsilon$): 314(4.50), 456(5.26), 586(4.07), 628(3.78) nm.
IR (KBr): approx. 1100 cm$^{-1}$ (perchlorate bands and W=O bands are under porphyrin bands).

EXAMPLE 9/1

Preparation of perchloratooxo(2,3,7,8,12,13,17,18,-octaethyl porphyrinato)tungsten (V), WO(OEP)OClO$_3$ A solution of 222 mg (0.15 mmole) [WO(OEP)]$_2$O in 30 ml CHCl$_3$ was agitated overnight with 3 ml perchloric acid (7% aqueous solution). The solvent was removed under gentle heating and the residue washed neutral with distilled water. Crystallization from toluene yielded 215 ml (86%) WO(OEP)OClO$_3$ as violet, metallic shiny platelets.
C$_{36}$H$_{44}$N$_4$O$_5$WCl (832.1).
Cal.: C 51.97 H 5.33 N 6.73.
Found: C 51.32 H 5.47 N 7.07.
UV/VIS ($\lambda$ max, log $\epsilon$): 328(4.52), 438(4.94), 562(4.00), 598(3.83) nm.
IR (KBr): approx. 1100 cm$^{-1}$ (W=O band is under the porphyrin bands).
MS (FD): 831 ($^{184}$WO(OEP)OClO$_3^+$), 732 ($^{184}$WO(OEP)$^+$).

EXAMPLE 10/1

Preparation of $\mu$-oxobis[oxo{5,10,15,20-tetra(p-methoxy phenyl)porphyrinato}tungsten (V)], [WO(TAP)]$_2$O A solution of 258 mg (0.5 mmole) WBr$_5$ in 30 ml benzonitrile was heated 1.5 hours under reflux and kept boiling another 3.5 hours after the addition of 170 mg (0.25 mmole) H$_2$(TAP). After the solvent had been distilled off in a high vacuum, the residue was taken up in CHCl$_3$ and chromatographed on Al$_2$O$_3$ (activity II, basic, 2.6×4.5 cm).

1st fraction: reddish violet H$_2$(TAP) (eluent: CH$_2$Cl$_2$)
2nd fraction: green WO(TAP)X (eluent: CH$_2$Cl$_2$/MeOH 99/1) 3d fraction: green WO(TAP)X (eluent: CH$_2$Cl$_2$/MeOH 95/5)

Since fractions 2 and 3 exhibited the same bands in the UV/VIS spectrum, they were combined and the solvent distilled off in a vacuum. The residue was dissolved in CHCl$_3$, compounded with 20 ml diluted aqueous KOH and agitated 2 hours. The CHCl$_3$ was removed by gentle heating, the precipitated material filtered off and washed neutral with distilled water. 70 mg (15%) of small, green scales of [WO(TAP)]$_2$O were obtained.
UV/VIS ($\lambda$ max, log $\epsilon$): 318(4.76), 450(5.54), 470(5.07), 588(4.15), 632(4.20), 672(3.99) nm.
IR (KBr): 650, 719 cm$^{-1}$ (typical for $\mu$-oxo systems).

EXAMPLE 11/1

Preparation of $\mu$-oxobis[oxo(2,3,7,8,12,13,17,18-octaethyl porphyrinato)tungsten(V)], [WO(OEP)]$_2$O 641 mg (1.2 mmole) H$_2$(OEP), 1.3 g (2.2 mmoles) WBr$_5$ were heated to a boil under agitation in 75 ml 1,2,4-trichlorobenzene in a 100 ml two-neck flask with reflux condenser and nitrogen introduction tube. Continously taken specimens were examined with a UV/VIS spectroscope. The spectra after 3 h and 4.5 h reaction time did not differ and showed only slight traces of free porphyrin. The reaction was stopped and the solvent removed in a high vacuum. The dark brown residue was taken up in CH$_2$Cl$_2$ and filtered. It was chromatographed on Al$_2$O$_3$ (activity III-n, 3.8×13 cm):
1st fraction, bright greenish blue, gradually turning to red after leaving the column, H$_2$(OEP), 10 mg, eluent CH$_2$Cl$_2$;
2nd fraction, green, eluent CH$_2$Cl$_2$/MeOH 95:5, MeOH portion gradually increased to 8%.

The 2nd fraction was condensed by evaporation until dry, taken up in 40 ml CH$_2$Cl$_2$ and agitated 18 h with a solution of 2 g KOH in 20 ml water. The solvent was removed by gentle heating, the precipitated complex was filtered off and washed neutral with distilled water. Crystallization from CH$_2$Cl$_2$/toluene yield 764 mg (86%) μ-oxo complex [WO(OEP)]$_2$O as reddish violet, finely crystalline powder.

C$_{72}$H$_{88}$N$_8$O$_3$W$_2$ (1481.2).

UV/VIS (λ max, log ε): 366(4.74), 430(5.09), 558(4.11), 660(3.32) nm.

IR (KBr): 646, 725 cm$^{-1}$ (typical for -oxo systems).

EXAMPLE 12

Preparation of acetatooxo(2,3,7,8,12,13,17,18-octaethyl porphyrinato)tungsten (V), WO(OEP)OAc A solution of 222 mg (0.15 mmole) [WO(OEP)]$_2$O in 30 ml CHCl$_3$ was agitated overnight with 2 ml glacial acetic acid and 50 mg sodium acetate. Then, the solvent and parts of the glacial acetic acid were removed by slight warming. Washing with distilled water freed the complex of adhering acetic acid and sodium acetate. After drying in a vacuum and crystallization from toluene, 202 mg (85%) WO(OEP)OAc resulted as shimmering violet, platelet-shaped crystals.

C$_{38}$H$_{47}$N$_4$O$_3$W (791.67).

Cal.: C 57.65 H 5.98 N 7.08.

Found: C 56.95 H 5.63 N 7.15.

UV/VIS (λ max, log ε): 324(4.45), 442(5.01), 565(4.00), 600(3.77) nm.

IR (KBr): 1660 (asymm. COO), 935 (W=O) cm$^{-1}$.

MS (FD): 791 ($^{184}$WO(OEP)OAc+).

EXAMPLE 3

Preparation of chlorooxo(5,10,15,20-tetraphenyl porphyrinato)tungsten (V), WO(TPP)Cl A solution of 246 mg (0.15 mmole) [WO(TPP)]$_2$O in 30 ml CHCl$_3$ was agitated overnight with 4 ml 37% aqueous hydrochloric acid. After the solvent had been evaporated, the residue was washed neutral with distilled water. Crystallization from toluene yielded 229 mg (90%) WO(TPP)Cl as dark green, metallic shimmering crystals.

C$_{44}$H$_{28}$N$_4$OWCl (832.1).

Cal: C 62.32 H 3.33 N 6.61.

Found: C 64.5 H 3.41 N 6.84.

UV/VIS (λ max, log ε): 316(4.57), 466(5.23), 600(3.95), 632(3.90) nm.

IR: 950 cm$^{-1}$ (W=O).

MS (FD): 847 ($^{184}$WO(TPP)Cl+), 812 ($^{184}$WO(TPP)+).

EXAMPLE 14

Preparation of methoxo-oxo[5,10,15,20-tetra(p-chlorophenyl)-prophyrinato] tungsten (V), WO(Tp-ClPP)OMe 316 mg (0.164 mmole) [WO(Tp-ClPP)]$_2$O were dissolved in 30 ml CHCl$_3$ and heated to a boil with 20 ml MeOH. Thereafter, the solvent was removed in a vacuum and the residue recrystallized from MeOH. 240 mg (75%) green platelets of the methoxo complex were obtained.

C$_{45}$H$_{27}$N$_4$Cl$_4$O$_2$W (981.4).

Cal.: C 55.08 H 2.75 N 5.71.

Found: C 52.46 H 2.36 N 5.46.

(Substance still contained aluminum oxide, since prepared from μ-oxo complex).

UV/VIS (λ max, log ε): 324(4.52), 444(4.79), 466(5.35), 578(4.04), 620(3.83) nm.

IR (KBr): 2795 (OMe), 920 (W=O) cm$^{-1}$.

MS (FD): 979 ($^{184}$WO(Tp-ClPP)OMe+).

EXAMPLE 15

Preparation of acetatooxo[5,10,15,20-tetra(p-tolyl) porphyrinato]-tungsten(V), WO(TTP)OAc A solution of 263 mg (0.15 mmoles) [WO(TTP)]$_2$O in 30 ml CHCl$_3$ was compounded with 2 ml glacial acetic acid as well as 50 mg sodium acetate and agitated overnight. The solvent and parts of the acetic acid were removed by gentle heating. The residue was freed of the sodium acetate and adhering acetic acid by washing with distilled water, dried in a vacuum and crystallized from toluene. 248 mg (99%) WO(TTP)OAc were obtained as finely crystalline, dark green crystal powder.

C$_{50}$H$_{39}$N$_4$O$_3$W.

Cal.: C 64.73 H 4.24 N 6.04.

Found: C 67.17 H 4.29 N 6.48.

UV/VIS (λ max, log ε): 306(4.49), 456(5.27), 590(3.96), 632(3.90) nm.

IR (KBr): 1660 (assym. COO), 950 (W=O) cm$^{-1}$.

MS (FD): 868 ($^{184}$WO(TTP)+).

EXAMPLE 16

Preparation of chlorooxo[5,10,15,20-tetra(p-tolyl)-porphyrinato]tungsten (V), WO(TTP) Cl A solution of 263 mg (0.15 mmole) [WO(TTP)]$_2$O in 30 ml CHCl$_3$ was agitated overnight with 4 ml 37% aqueous hydrochloric acid. After the solvent had been evaporated, the residue was washed neutral with distilled water. Crystallization from toluene yielded 255 mg (94%) WO(TTP)Cl as dark green, scaly crystals.

C$_{48}$H$_{36}$N$_4$OWCl (904.14).

Cal.: C 63.74% H 4.01% N 6.20%.

Found: C 66.79% H 3.99% N6.56%.

UV/VIS (λ max, log ε): 314(4.60), 470(5.26), 604(3.95), 650(4.00) nm.

IR: 950 cm$^{-1}$, (W=O).

MS: 904, ($^{184}$WO(TTP)Cl).

EXAMPLE 17

Preparation of perchloratooxo[5,10,15,20-tetra(p-tolyl)-porphyrinato]-tungsten (V), WO(TTP)OClO$_3$ A solution of 264 mg (0.15 mmole) [WO(TTP)]$_2$O in 30 ml CHCl$_3$ was agitated 18 h with 4 ml aqueous 7% perchloric acid. The solvent was evpaporated under slight heating and the residue washed neutral with distilled water. Crystallization from toluene yielded 247 mg (85%) WO(TTP)ClO$_4$ as deep violet, metallic shiny platelets.

C$_{48}$H$_{36}$N$_4$O$_5$WCl (968.1).

Cal.: C 59.55 H 3.75 N 5.79.

Found: C 61.78 H 3.84 N 6.40.

UV/VIS (λ max, log ε): 308(4.49), 458(4.92), 632(3.72), 650(4.00) nm.

IR (KBr): approx. 1100 cm$^{-1}$ (band for coordinated perchlorate is under porphyrin bands).

MS (FD): 868 ($^{184}$WO(TTP)+).

Further variations and modifications will become apparent to those skilled in the art from the foregoing and are intended to be encompassed by the appended claims.

German priority application P 37 09 829.2-42 is relied on herein.

nyl amino, amino sulfonyl, amino sulfonyl containing one or two $C_1$-$C_6$-alkyl groups, by $C_1$-$C_6$-alkoxysulfonyl (—$SO_2$—O—$C_1$-$C_6$-alkyl), sulfo or $C_1$-$C_6$-alkanesulfonyl or two methylene dioxy groups wherein the complex in the case of tungsten oxo complexes optionally carries an anion on the central atom from the group $F^-$, $Cl^-$, $Br^-$, $I^-$, $CH_3O^{13}$, $C_2H_5O^-$, $C_3H_7O^-$, t-$C_4H_9O^-$, $HO^-$, $AcO^-$, $SCN^-$, $CN^-$, $C_6H_5O^-$.

Table of Results

| Example Nr. | Olefine (Mole(s)) | $H_2O_2$ (Mole(s)) | Catalyst | (Mole(s)) | Reaction Conditions Solvent (ml) | Temp. (°C.) | Time (h) | Conversion $H_2O_2$ | Selectivity (%) |
|---|---|---|---|---|---|---|---|---|---|
| 8 | 1,5-COD (36) | 85% aq. (12) | OW(Tp-CLPP)0CLO$_3$ | $12 \times 10^{-2}$ | nPAC | 60 | 1 | 87,5 | 53,4 |
| 9/1 | 1,5-COD (36) | 85% aq. (12) | OW(OEP)OCLO$_3$ | $12 \times 10^{-2}$ | n-PAC | 60 | 1 | 96,7 | 72,1 |
| 9/2 | 1,5-COD (36) | 85% aq. (12) | from Nr. 9/1 (recycled) | $12 \times 10^{-2}$ | n-PAC | 60 | 1 | 92,4 | 86,1 |
| 10/1 | 1,5-COD (18) | 85% aq. (6) | [OW(TAP)]$_2$O | $6 \times 10^{-2}$ | n-PAC | 60 | 1 | 90,5 | 62,1 |
| 10/2 | 1-5-COD (18) | 85% aq. (6) | from Nr. 10/1 (recycled) | $6 \times 10^{-2}$ | n-PAC | 60 | 1 | 88,7 | 70,9 |
| 11/1 | 1,5-COD (36) | 85% aq. (12) | [OW(OEP)]$_2$O | $12 \times 10^{-2}$ | n-PAC | 60 | 1 | 97,9 | 33,7 |
| 11/2 | 1,5-COD (36) | 85% aq. (12) | from Nr. 11/1 (recycled) | $12 \times 10^{-2}$ | tert.- | 60 | 3 | 97,3 | 94,2 |
| 12 | 1,5-COD (36) | 85% aq. (12) | OW(OEP)OAc | $12 \times 10^{-2}$ | n-PAC | 60 | 3 | 99,4 | 69,1 |
| 13 | 1,5-COD (36) | 85% aq. (12) | OW(TPP)CL | $12 \times 10^{-2}$ | n-PAC | 60 | 4 | 25,9 | 64,4 |
| 14 | 1,5-COD (36) | 85% aq. (12) | OW(Tp-CLPP)OMe | $12 \times 10^{-2}$ | n-PAC | 60 | 1 | 94,5 | 66,7 |
| 15 | 1,5-COD (36) | 85% aq. (12) | OW(TTP)OAc | $12 \times 10^{-2}$ | n-PAC | 60 | 1 | 93,6 | 71,2 |
| 16 | 1,5-COD (36) | 85% aq. (12) | OW(TTP)CL | $12 \times 10^{-2}$ | n-PAC | 60 | 4 | 95,6 | 81,2 |
| 17 | 1,5-COD (36) | 85% aq. (12) | OW(TTP)OCLO$_3$ | $12 \times 10^{-2}$ | n-PAC | 60 | 1 | 97,0 | 49,2 |
| 18 | 1,5-COD | 30% aq. | OW(TPP)Br | $12 \times 10^{-2}$ | t-Butanol | 60 | 4 | 94,7 | 60,2 |

We claim:

1. Method for the catalytic epoxidation of olefins with hydrogen peroxide, comprising reacting an olefin in a homogeneous phase reaction medium or in a two-phase reaction medium system with a sufficient amount of a source of hydrogen peroxide in the presence of
   tungsten oxo complexes or
   a binuclear compound of the type μ-oxobis(porphyrinato oxo tungsten (V)) or
   an oxo peroxo compound of the type cis-oxo peroxo tungsten (VI) porphyrin or
   a cis-dioxo porphyrinato tungsten (VI) complex with
   octaethyl porphyrin or
   5,10,15,20-tetraphenyl porphyrin or
   5,10,15,20-tetra(4-pyridyl)porphyrin
as ligands in which hydrogen atoms or free electron pairs are optionally substituted once or several times on the phenyl or pyridyl groups by halogen, hydroxy, carboxy, cyano, rhodano, nitro, $C_1$-$C_6$-alkyl, trihalomethane, $C_1$-$C_6$-alkoxy, $C_1$-$C_6$-alkane sulfonyloxy, amino carbonyl, amino carbonyl containing one or two $C_1$-$C_6$-alkyl groups, by $C_1$-$C_6$-alkyl carbonyl, amino, Di-$C_1$-$C_6$-alkyl amino, ($C_1$-$C_6$-alkyl)$_3$N, $C_1$-$C_6$-alkanoyl amino, $C_1$-$C_6$-alkyl-$C_1$-$C_6$-alkanoyl amino, $C_1$-$C_6$-alkane sulfonyl amino, $C_1$-$C_6$-alkyl-$C_1$-$C_6$-alkane sulfo- 2. Method according to claim 1, wherein an organic solvent or a solvent mixture is used as reaction medium which permits a transition from hydrogen peroxide used as an aqueous solution into the organic phase.

3. Method according to claim 1 wherein when water-free hydrogen peroxide is used and an organic solvent is used which is an alkyl ester or cycloalkyl ester of saturated aliphatic carboxylic acids with a carbon number of 4-8.

4. Method according to claim 1 wherein the reaction occurs in the presence of 0.1 to 10 moles, in relation to 1 mole of the catalyst, of a heterocyclic amine compound from the family of pyridine or imidazole.

5. Method according to claim 1 to 3 characterized wherein the reaction occurs inthe presence of 0.5 to 5 moles, in relation to 1 mole of the catalyst, of a heterocyclic amine compound from the family of pyridine or imidazole.

6. Method according to claim 4, characterized in that γ-picoline or imidazole is used.

7. Method according to claim 5 wherein in that γ-picoline or imidazole is used.

8. Method according to claim 1 wherein the catalyst used for epoxidation is recycled for other epoxidations after separation of the reaction mixture.

* * * * *